(12) United States Patent
Folta

(10) Patent No.: US 10,876,109 B2
(45) Date of Patent: Dec. 29, 2020

(54) METHODS OF IDENTIFYING BIOLOGICALLY ACTIVE RANDOM PEPTIDES IN PROKARYOTIC CELLS AND LIBRARIES OF PROKARYOTIC CELLS EXPRESSING CANDIDATE BIOLOGICALLY ACTIVE RANDOM PEPTIDES

(71) Applicant: University of Florida Research Foundation, Inc., Gainesville, FL (US)

(72) Inventor: Kevin Michael Folta, Archer, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/393,281

(22) Filed: Apr. 24, 2019

(65) Prior Publication Data

US 2019/0382756 A1 Dec. 19, 2019

Related U.S. Application Data

(63) Continuation-in-part of application No. 15/790,639, filed on Oct. 23, 2017, and a continuation-in-part of application No. PCT/US2016/058573, filed on Oct. 25, 2016, which is a continuation-in-part of application No. PCT/US2016/028797, filed on Apr. 22, 2016.

(60) Provisional application No. 62/506,322, filed on May 15, 2017, provisional application No. 62/152,189, filed on Apr. 24, 2015.

(51) Int. Cl.
    *C12N 15/10* (2006.01)

(52) U.S. Cl.
    CPC .............................. *C12N 15/1082* (2013.01)

(58) Field of Classification Search
    CPC .................................................. C12N 15/1082
    See application file for complete search history.

(56) References Cited

U.S. PATENT DOCUMENTS

| | | |
|---|---|---|
| 2004/0126762 A1 | 7/2004 | Morris et al. |
| 2005/0059135 A1 | 3/2005 | Klein et al. |
| 2007/0209085 A1 | 9/2007 | Wu et al. |
| 2011/0162109 A1 | 6/2011 | Himanen et al. |
| 2011/0184157 A1 | 7/2011 | Yu et al. |
| 2015/0159166 A1 | 6/2015 | Archibald et al. |

FOREIGN PATENT DOCUMENTS

| | | |
|---|---|---|
| GB | 2130219 A | 5/1984 |
| WO | WO 00/05406 A1 | 2/2000 |
| WO | WO 2012/135385 A1 | 10/2012 |
| WO | WO 2016/172445 A2 | 10/2016 |

OTHER PUBLICATIONS

International Search Report and Written Opinion in International application No. PCT/US16/28797 dated Oct. 24, 2016, 21 pages.

(Continued)

*Primary Examiner* — Robert H Havlin
(74) *Attorney, Agent, or Firm* — Thomas | Horstemeyer, LLP

(57) ABSTRACT

The present disclosure provides methods and systems for identifying biologically active random peptides (BARPs) in prokaryotic cells, such as bacterial cells, and libraries of transformed bacterial cells, where each cell/colony expresses a different candidate BARP.

12 Claims, 5 Drawing Sheets

Specification includes a Sequence Listing.

SEQ ID NO: 1

Vector Seq → ATGGCCTGTNNNNNNNNNNNNNNNNNNTGTTAG ← Vector Seq
(GGC) ----sequence of random nt's in multiples of 3---
Start Ala (or Gly) Cys (e.g., 18 random nucleotides corresponding to 6 random codons) Cys Stop Vector Seq

(56) References Cited

OTHER PUBLICATIONS

International Search Report and Written Opinion in International application No. PCT/US16/58573 dated Jan. 19, 2017, 21 pages.
GenBank Accession No. JP152896, TSA: Ipomoea batatas Contig_48308.Ipbalsr mRNA sequence, May 7, 2012 [online], [Retrieved on Oct. 14, 2016], Retrieved from the internet <URL: https://www.ncbi.nlm.nih.gov/nuccore/JP152896>, 1 page.
Aspiras, Marcelo B., et al. "ComX activity of *Streptococcus* mutans growing in biofilms", FEMS Microbiology Letters 238 (2004), 167-174.

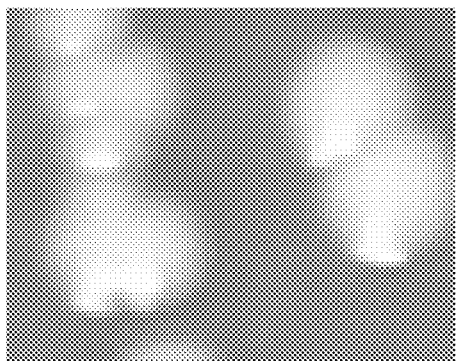
FIG. 2D
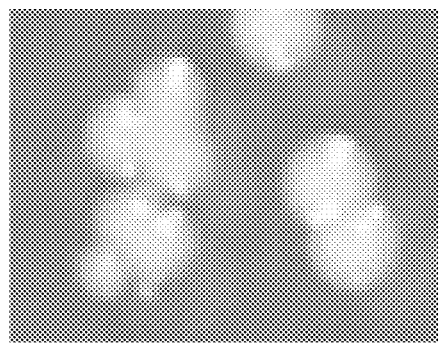
FIG. 2H
FIG. 2C
FIG. 2G
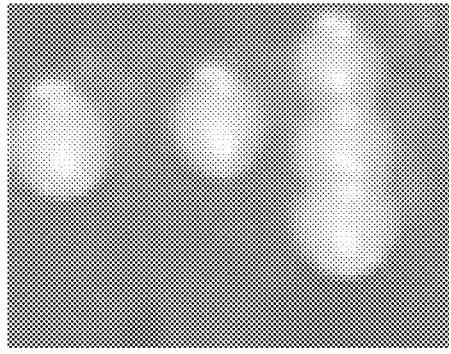
FIG. 2B
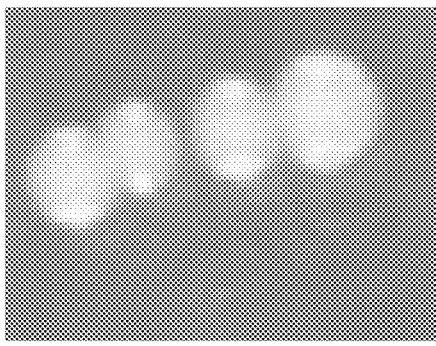
FIG. 2F
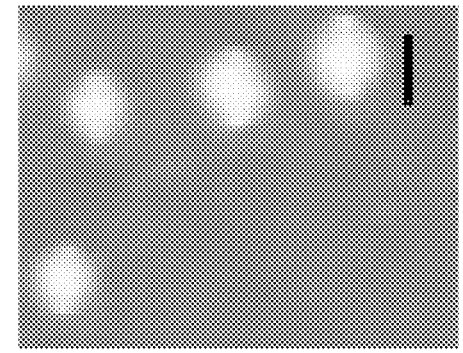
FIG. 2A
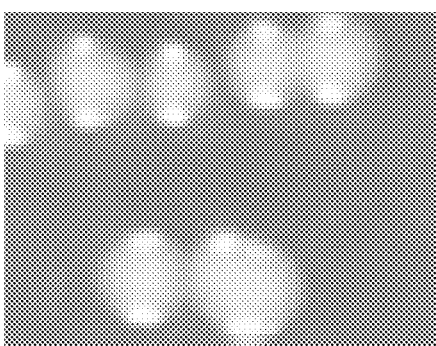
FIG. 2E

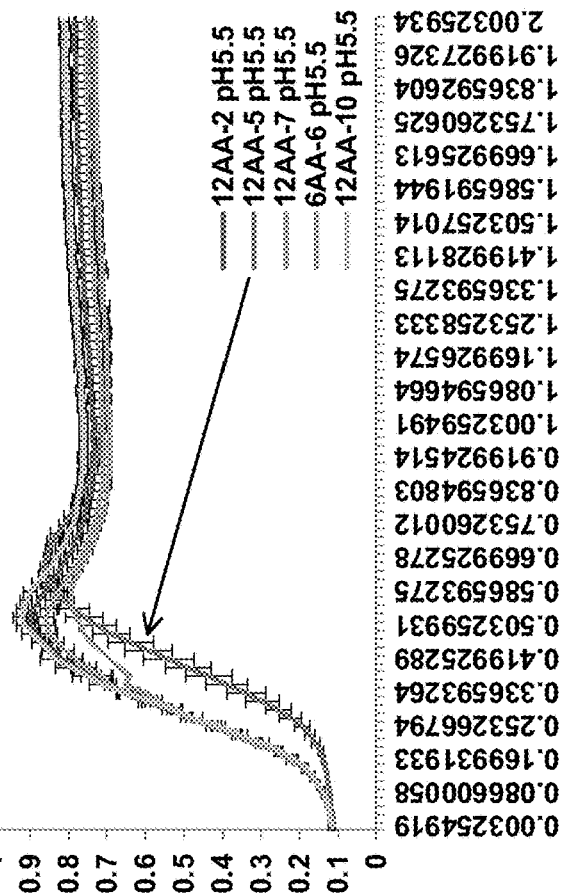
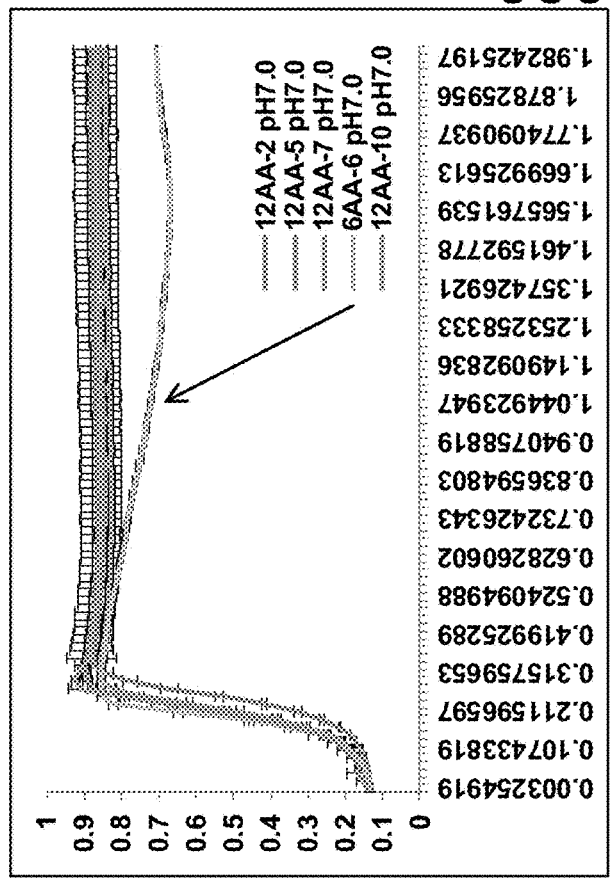
FIG. 4A
FIG. 4B

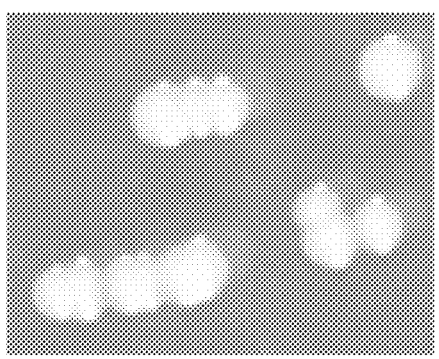
FIG. 5D
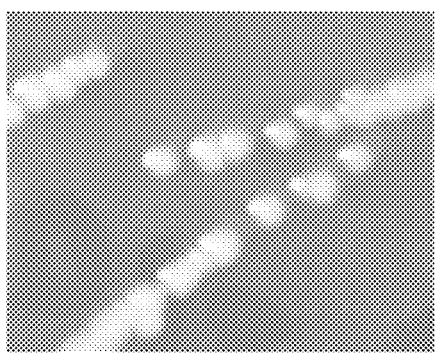
FIG. 5C
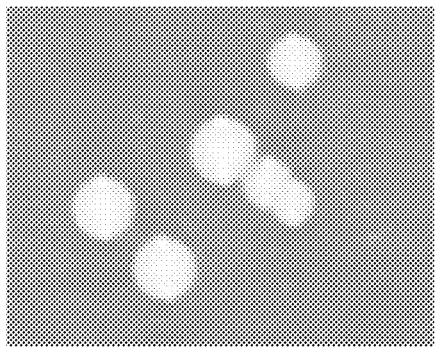
FIG. 5B
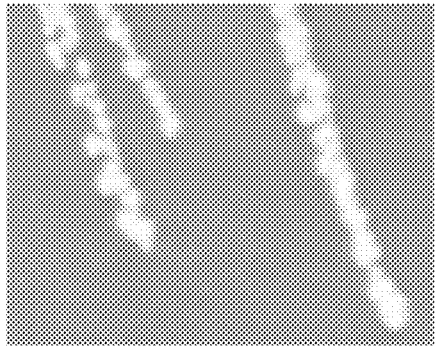
FIG. 5A
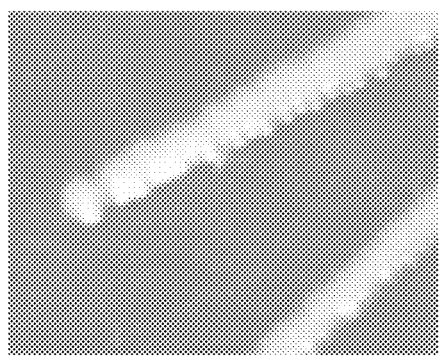
FIG. 5H
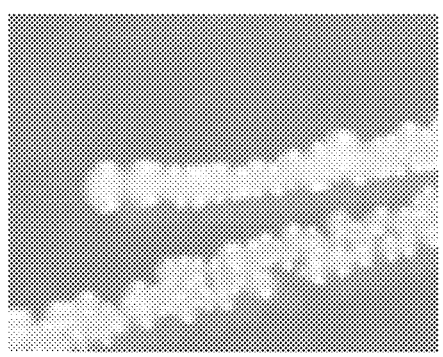
FIG. 5G
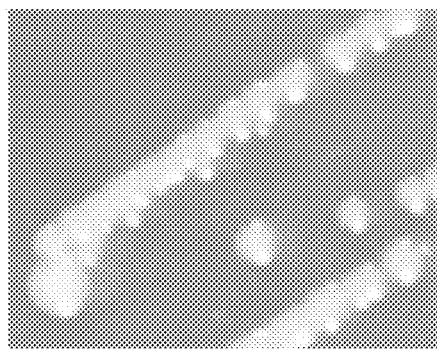
FIG. 5F
FIG. 5E // METHODS OF IDENTIFYING BIOLOGICALLY ACTIVE RANDOM PEPTIDES IN PROKARYOTIC CELLS AND LIBRARIES OF PROKARYOTIC CELLS EXPRESSING CANDIDATE BIOLOGICALLY ACTIVE RANDOM PEPTIDES

CROSS-REFERENCE TO RELATED APPLICATIONS

This application is a continuation-in-part of PCT Application No. PCT/US2016/058573, filed Oct. 25, 2016 and entitled "METHODS OF IDENTIFYING BIOLOGICALLY ACTIVE RANDOM PEPTIDES IN PROCARYOTIC CELLS AND LIBRARIES OF PROCARYOTIC CELLS EXPRESSING CANDIDATE BIOLOGICALLY ACTIVE RANDOM PEPTIDES," which is hereby incorporated by reference herein in its entirety. This application is also a continuation-in-part of co-pending U.S. patent application Ser. No. 15/790,639, filed Oct. 23, 2017 and entitled "METHODS OF IDENTIFYING BIOLOGICALLY ACTIVE RANDOM PEPTIDES IN PLANTS AND LIBRARIES OF PLANTS EXPRESSING CANDIDATE BIOLOGICALLY ACTIVE RANDOM PEPTIDES," which claims the benefit of and priority to U.S. Provisional Patent Application No. 62/506,322, having the same title and filed on May 15, 2017; where the '639 application is also a continuation-in-part of PCT Application No. PCT/US2016/028797, having the same title and filed Apr. 22, 2016, which also claimed priority to and the benefit of U.S. Provisional Patent Application No. 62/152,189 of the same title, filed on Apr. 24, 2015, all of which are incorporated by reference herein in their entireties.

SEQUENCE LISTING

This application contains a sequence listing filed in electronic form as an ASCII.txt file entitled 222109-2320_ST25.txt created on Oct. 24, 2016 and having a size of 7 KB. The content of the sequence listing is incorporated herein in its entirety.

BACKGROUND

Scientists use a process called chemical genomics to identify key regulatory molecules that influence specific biological processes. Chemical genomics involves the identification of novel applications for known compounds. The approach applies individual chemicals from 'libraries' of compounds to an animal, plant, bacterium or fungus, and then searches for changes. In plants and animals this approach is used to identify new potential drugs or growth regulators that are neither anticipated nor designed; instead, they are a chance consequence of chemical interaction that triggers a reproducible response. Chemical genomics screens test a libraries of thousands of compounds to identify those that elicit a desired effect.

Using a technique such as chemical genomics to screen libraries of peptides for biological activity in prokaryotic organisms, such as bacteria, involves time consuming synthesis and testing steps and presents challenges. Alternative approaches, such as site directed mutagenesis require specific targets and engineering aimed at designing specific mutations for a desired effect. Some methods are tailored specifically to eukaryotic systems. Thus, the field needs alternative methods for producing large libraries of potential active compounds and methods for screening libraries of compounds for biological activity in prokaryotes and identifying novel biologically-active compounds.

SUMMARY

The present disclosure provides methods for identifying biologically active random peptides (BARPs) in prokaryotic cells and bacterial cells and libraries of transformed bacterial cells.

In embodiments, methods of identifying BARPs in bacterial cells include providing a library having a plurality of different test nucleic acid sequences. The library includes a plurality of different test nucleic acid sequences encoding a plurality of candidate BARPs, where each test nucleic acid sequence includes nucleic acids encoding a start codon, a random sequence of 6 to 20 amino acids representing a candidate BARP, a pair of cysteines flanking the random sequence of amino acids, and a stop codon. The methods further include creating a library of recombination vectors from the library of test nucleic acid sequences, where each vector includes a test nucleic acid sequence from the library and a nucleic acid sequence encoding a selectable marker operably linked to the test nucleic acid sequence. The method includes transforming a plurality of phenotypically homogenous bacterial cells of the same species and/or strain with the library of recombination vectors. Then, the bacterial cells are screened for the presence of the selectable marker to select bacterial cells with the selectable marker to produce a library of transformed bacterial cells, where each bacterial cell includes a recombination vector from the library and identification of the selectable marker indicates expression of a candidate BARP by the bacterial cell. Finally, the library of recombinant bacterial cells is observed and screened throughout development for the occurrence of a new phenotype, where the new phenotype is discernible from the phenotype of a wild type bacterial cell/colony and where the presence of the new phenotype indicates the candidate BARP is responsible for the new phenotype.

In embodiments, methods of identifying BARPs in prokaryotic cells include providing a library of test nucleic acid sequences, as described above. The library includes a plurality of different test nucleic acid sequences encoding a plurality of candidate BARPs, where each test nucleic acid sequence includes nucleic acids encoding a start codon, a random sequence of amino acids representing a candidate BARP, and a stop codon. The methods further include creating a library of recombination vectors from the library of test nucleic acid sequences, where each vector includes a test nucleic acid sequence from the library and a nucleic acid sequence encoding a selectable marker operably linked to the test nucleic acid sequence. The method includes transforming a plurality of phenotypically homogenous prokaryotic cells of the same species and/or strain (e.g., bacterial cells of the same species and strain) with the library of recombination vectors. Then, the prokaryotic cells are screened for the presence of the selectable marker to select prokaryotic cells with the selectable marker to produce a library of transformed prokaryotic cells, where each prokaryotic cell includes a recombination vector from the library and identification of the selectable marker indicates expression of a candidate BARP by the prokaryotic cell. Finally, the library of recombinant prokaryotic cells is observed and screened throughout development for the occurrence of a new phenotype, where the new phenotype is discernible from the phenotype of a wild type prokaryotic cell and where the presence of the new phenotype indicates the candidate BARP is responsible for the new phenotype.

Embodiments of the present disclosure also include a library of transformed bacterial cells including a plurality of bacterial cells of the same species and strain, each bacterial cell including a recombination vector, where a majority of the bacterial cells have a different recombination vector than the other cells in the library. In embodiments, each recombination vector in the library includes: a test nucleic acid sequence encoding a candidate biologically active random peptide (BARP), where each test nucleic acid sequence comprises nucleic acids encoding a start codon, a random sequence of amino acids representing the candidate BARP, and a stop codon; and a nucleic acid sequence encoding a selectable marker operably linked to the test nucleic acid sequence, where the test nucleic acid sequence in a plurality of the vectors encodes a different random sequence of amino acids from the other vectors and where the plurality of bacterial cells is phenotypically homogeneous in the absence of the recombination vector.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 2A-L are digital images illustrating the effect of some of the tested BARPs on colony morphology of *S. mutans*. FIG. 2A shows the colony morphology of *S. mutans* UA159 with Pcomx::lacZ transformed with RBS6AA-11 constructed on pDL278GW vector as a control. Colonies are small and rough, indicating normal growth. FIGS. 2B-2L illustrate large and mucoid colony morphology of *S. mutans* UA159 with pcomX::lacZ transformed with different small peptides: 12AA-2 (2B), 12AA-5 (2C), 12AA-6 (2D), 12AA-7 (2E), 12AA-10 (2F), 12AA-11 (2G), RBS6AA-1 (2H), RBS6AA-10 (2I), RBS6AA-12 (2J), RBS12AA-5 (2K), RBS12AA-9 (2L). Scale bar=1 mm.

FIG. 3A illustrates *S. mutans* UA159 with PcomX::lacZ transformed with 6AA-6 constructed on pDL278GW vector as a control. The colonies had bright blue color, indicating the full competency. FIGS. 3B-D illustrate *S. mutans* UA159 with pcomX::lacZ transformed with 12AA-1 (3B), 12AA-3 (3C) and 12AA-4 (3D), respectively. The colonies had a light blue color ("less blue" phenotype) indicating the reduction of competency. Scale bar=1 mm. Blue color does not show on black/white images.

FIGS. 4A-4B are graphs illustrating growth of *S. mutans* strain PcomX::lacZ transformed with small peptides (6AA-6, 12AA-2, 12AA-5, 12AA-7 and 12AA-10) and grown in BHI medium at PH 7.0 (FIG. 4A) or PH 5.5 (FIG. 4B) for 2 days with the initiation OD600 0.5. FIG. 4A shows that, at PH7.0, the control strain transformed with 6AA-6 peptide has a reduction of bacterial growth, while strains transformed with 12AA-2, 12AA-5, 12AA-7 and 12AA-10 have prolonged bacterial growth. FIG. 4B demonstrates that, at PH5.5, all strains have similar growth curve except the strain transformed with 12AA-5, which has a longer lagging time.

FIGS. 5A-5H illustrate colony morphology of *S. mutans* strain transformed plasmids extracted from original isolates. FIG. 5A illustrates colonies of *S. mutans* UA159 with Pcomx::lacZ transformed with a plasmid encoding the peptide 6AA-6 isolated from the original screening and used here as control. Colonies are rough and small, which is the normal phenotype. FIGS. 5B-5H illustrate colonies of *S. mutans* UA159 with Pcomx::lacZ transformed with plasmids of peptide 12AA-2 (5B), 12AA-6 (5C), 12AA-11 (5D), RBS6AA-1 (5E), RBS6AA-10 (5F), RBS6AA-12 (5G), and RBS12AA-9 (5H), all of which are isolated from the original screening. Colonies are not rough and small, but are larger and mucoid. Scale bar=1 mm.

DETAILED DESCRIPTION

Figure 1:
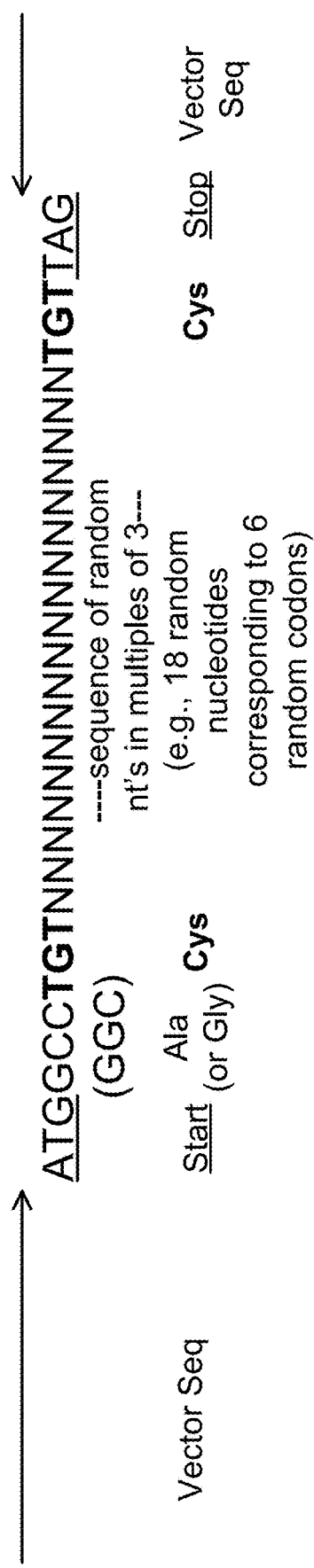
FIG. 1 illustrates an embodiment of a degenerative DNA oligonucleotide sequence (SEQ ID NO: 1, where N can be A, G, C, or T, such that each group of three N's "NNN" encodes an amino acid) used to generate a library of different sequences for use in a recombination-cloning system that then can be individually installed into plants, each capable of making a discrete peptide.
Figure 2I:
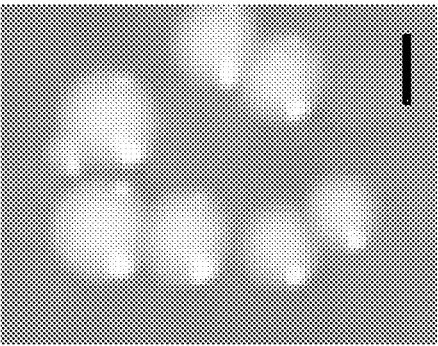
Figure 2J:
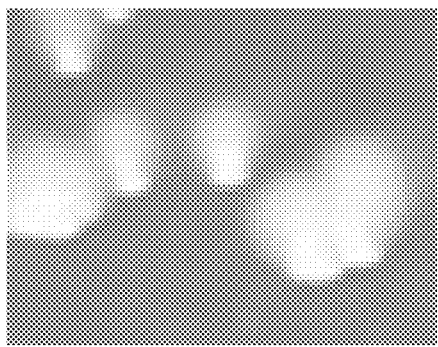
Figure 2K:
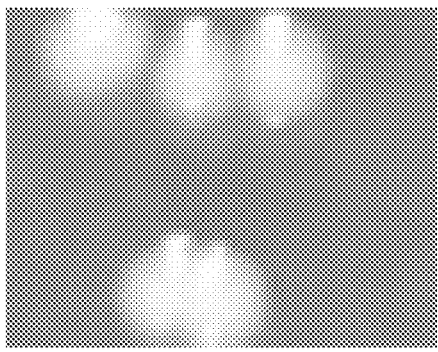
Figure 2L:
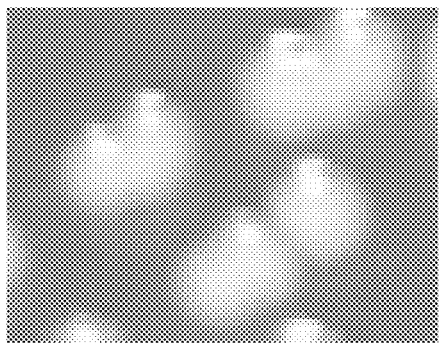

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification that are incorporated by reference, by notation in the application, are incorporated by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing the disclosed subject matter, the following terminology will be used in accordance with the definitions set forth below.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism and its regulatory sequences.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. A "transformed" cell is thus a cell transfected with a nucleic acid sequence. The term "transformation" refers to the introduction of a nucleic acid (e.g., DNA or RNA) into cells in such a way as to allow expression of the coding portions of the introduced nucleic acid. The term "transgene" refers to an artificial gene which is used to transform a cell of an organism, such as a bacterium or a plant.

As used herein, "transformation" or "transformed" refers to the introduction of a nucleic acid (e.g., DNA or RNA) into cells in such a way as to allow expression of the coding portions of the introduced nucleic acid.

As used herein a "transformed cell" is a cell transfected with a nucleic acid sequence.

As used herein, a "transgene" refers to an artificial gene which is used to transform a cell of an organism, such as a bacterium or a plant.

As used herein, "transgenic" refers to a cell, tissue, or organism that contains a transgene.

As used herein, "isolated" means removed or separated from the native environment. Therefore, isolated DNA can contain both coding (exon) and noncoding regions (introns) of a nucleotide sequence corresponding to a particular gene. An isolated peptide or protein indicates the protein is separated from its natural environment. Isolated nucleotide sequences and/or proteins are not necessarily purified. For instance, an isolated nucleotide or peptide may be included in a crude cellular extract or they may be subjected to additional purification and separation steps.

With respect to nucleotides, "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a variant of a CCD enzyme) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The term "expression" as used herein describes the process undergone by a structural gene to produce a polypeptide. It is a combination of transcription and translation. Expression generally refers to the "expression" of a nucleic acid to produce a polypeptide, but it is also generally acceptable to refer to "expression" of a polypeptide, indicating that the polypeptide is being produced via expression of the corresponding nucleic acid.

As used herein, the term "over-expression" and "up-regulation" refers to the expression of a nucleic acid encoding a polypeptide (e.g., a gene) in a transformed cell (e.g., transformed bacterial or other prokaryotic cell) at higher levels (therefore producing an increased amount of the polypeptide encoded by the gene) than the corresponding "wild type" cell (e.g., a substantially equivalent cell that is not transfected with the gene) under substantially similar conditions. Thus, to over-express or increase expression of a target nucleic acid refers to increasing or inducing the production of the target polypeptide encoded by the nucleic acid, which may be done by a variety of approaches, such as increasing the number of genes encoding for the polypeptide, increasing the transcription of the gene (such as by placing the gene under the control of a constitutive promoter), or increasing the translation of the gene, or a combination of these and/or other approaches. Conversely, "under-expression" and "down-regulation" refers to expression of a polynucleotide (e.g., a gene) at lower levels (producing a decreased amount of the polypeptide encoded by the polynucleotide) than in a "wild type" plant cell. As with over-expression, under-expression can occur at different points in the expression pathway, such as by decreasing the number of gene copies encoding for the polypeptide, inhibiting (e.g., decreasing or preventing) transcription and/or translation of the gene (e.g., by the use of antisense nucleotides, suppressors, knockouts, antagonists, etc.), or a combination of such approaches.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast DNA, bacterial genomic or plasmid DNA, or viral DNA, or may contain elements of more than one of these.

As used herein, the term "expression system" includes a biologic system (e.g., a cell based system) used to express a polynucleotide to produce a protein. Such systems generally employ a plasmid or vector including the polynucleotide of interest, where the plasmid of expression vector is constructed with various elements (e.g., promoters, selectable markers, etc.) to enable expression of the protein product from the polynucleotide. Expression systems use the host system/host cell transcription and translation mechanisms to express the product protein. Common expression systems include, but are not limited to, bacterial expression systems (e.g., *E. coli*), yeast expression systems, viral expression systems, animal expression systems, and plant expression systems.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences necessary for expression of the coding sequences of a nucleic acid are placed in the nucleic acid molecule in the appropriate positions relative to the coding sequence so as to effect expression of the coding sequence. This same terminology is sometimes applied to the arrangement of coding sequences and transcription control elements (e.g. promoters, enhancers, and termination elements), and/or selectable markers in an expression vector.

As used herein, the term "selectable marker" or "selective marker" refers to a gene whose expression allows one to identify cells and/or whole organisms (e.g., plants) that have been transformed or transfected with a vector containing the marker gene. For instance, a recombinant nucleic acid may include a selectable marker operably linked to a gene of interest and a promoter, such that expression of the selectable marker indicates the successful transformation of the cell with the gene of interest. Some examples of selectable markers include genes encoding for antibiotic resistance, genes encoding for fluorescence or other detectable signal. "Detectable" refers to the ability to perceive or distinguish a signal over a background signal. "Detecting" refers to the act of determining the presence of and recognizing a target or the occurrence of an event by perceiving a signal that indicates the presence of a target or occurrence of an event, where the signal is capable of being perceived over a background signal.

The terms "native," "wild type", or "unmodified" in reference to an organism (e.g., plant or cell), polypeptide, protein or enzyme, are used herein to provide a reference point for a variant/mutant of an organism, polypeptide, protein, or enzyme prior to its mutation and/or modification (whether the mutation and/or modification occurred naturally or by human design). Typically, the unmodified, native, or wild type organism, polypeptide, protein, or enzyme has an amino acid sequence that corresponds substantially or completely to the amino acid sequence of the polypeptide, protein, or enzyme as it typically/predominantly occurs in nature.

As used herein, the term "phenotypically homogenous" indicates that individual organisms of a group/population are phenotypically so similar as to be virtually indistinguishable. Thus, if a group of plants or bacterial cells of the same species is a "phenotypically homogenous population", although the individual organisms in the group may have some genetic variations resulting in subtle genetic differences (in other words, they may not be genetic clones), the visible and observable phenotypes (such as color, growth rate, flowering, leaf morphology, hardiness, light sensitivity, life cycle and the like) are essentially the same. In this way, any observed differences in phenotype in transformed individuals can be putatively associated with expression of the transgene.

As used herein, the term "library" refers to a collection of items (e.g., group of DNA sequences, peptides, group of chemical compounds, group of cells, group of organisms, etc.), where most of the individual items in the library differ from every other item (or substantially every other item; some small percentage of repeats may be unavoidable) in some aspect. For instance, in a library of peptides, each peptide in the library has a different peptide sequence (with allowances for a small percentage of randomly occurring duplicates).

The term "biologically active random peptide (BARP)" refers to a peptide fragment having a random sequence that has a biological activity, in that the peptide directly or indirectly affects a biological function. In embodiments a BARP may affect a biological function by an activity such as, but not limited to, binding an enzyme active site, blocking channels, destabilizing substrates, integrating with a biochemical or structural process, and the like. In the present disclosure, a random peptide with the potential to be biologically active is referred to as a "candidate BARP" or "potential BARP". However, such potential BARPs are also sometimes referred to herein as a BARP prior to screening for activity.

The term "phenotype", as used herein, refers to an organism's observable traits/characteristics resulting from the organism's genetic makeup (e.g., genotype) in combination with the environment.

Discussion

Embodiments of the present disclosure encompass methods of identifying biologically active random peptides (BARPs) in prokaryotic cells, methods of screening libraries of candidate BARPs for in vivo biological activity in prokaryotic cells, and libraries of transformed prokaryotic cells expressing candidate BARPs.

Prokaryotic cells, such as bacteria, represent a convenient system for screening for novel BARPs. Their small size, controllable culture conditions, small genome, and other factors offer advantages in such approaches. Although prokaryotic organisms exhibit phenotypic and developmental plasticity, rendering them well-suited for chemical genomics approaches, chemical genomics methods suffer from some of the drawbacks discussed above.

The methods of the present disclosure provide an alternative parallel approach to chemical genomics in the search for new growth regulators and other active peptides in prokaryotes. Instead of having to grow bacteria or other prokaryotic organisms and subsequently treat them with expensively synthesized chemicals (e.g., peptides), each prokaryotic cell (and colony formed from that cell) can be genetically altered to produce a novel peptide that may affect its own biology. Thus, instead of applying the chemical compound and looking for an effect, the methods of the present disclosure include the creation of a population of prokaryotes where each prokaryotic cell makes a novel compound (e.g., a bacterial library), which can then be screened for effects during all stages of growth and development. In this way, the individual organism (e.g., bacterial cell) tells observers which compound promotes biological consequences.

It is not believed that the approach of preparing large numbers of transgenic whole organism libraries for exploration of random peptide effects by inducing phenotypes has been extensively studied in many organism systems, including prokaryotes. In part this may be due to the fact that easily transformable fungi (e.g., yeast) have limited phenotypes, and complex eukaryotic organisms, such as animals, with a large number of potential phenotypes are difficult to transform. Plants and prokaryotic cells are relatively easily transformed, have a wide variety of observable phenotypes, are small, and can be grown in large numbers in a relatively small area, making them good candidates for this approach. The methods of the present disclosure are described with respect to prokaryotic cells, and are also adaptable to other organisms. Embodiments of the methods of the present disclosure for identifying novel BARPs will be described below primarily in reference to prokaryotic systems. Modification of the methods and systems described herein may be made to adapt such methods and systems for use in other systems, such as fungi and animals.

Systems

In embodiments, the methods of the present disclosure provide a way to screen for biologically active peptides, in vivo, by producing prokaryotic cells/colonies (e.g., bacteria), each expressing a novel, random peptide sequence, referred to as a candidate BARP. This technology can have profound effects in identification of new peptide sequences that can modulate bacterial growth and development and potentially find use as new, environmentally sound products, such as probiotics, antibiotics, environmentally remediating bacteria, and the like.

The present disclosure thus provides an innovative pipeline to rapidly discover new drugs and growth regulators in prokaryotic systems. Generally described, the present disclosure provides methods to screen populations of any transformable organism for BARPs. Small peptides have the potential to integrate into a wide set of biological processes and thus represent good candidates for discovering new biologically active compounds. The methods of the present disclosure exploit flexibility in molecular cloning techniques and degenerate sequence amplification to produce libraries of random nucleic acid test sequences encoding potential BARPs and using these test sequences to generate populations/libraries of prokaryotes where each cell/colony expresses a different small peptide (e.g., differing in amino acid composition and/or length). The methods below will be discussed with respect to bacterial systems, but it will be understood that the methods can be applied to other prokaryotic systems by a skilled artisan using the methodologies of the present disclosure.

In the libraries created in the methods of the present disclosure, one or more of the individual peptide sequences (candidate BARPs) may affect biological function (e.g., may prove to be an actual BARP) by binding to enzyme active sites, blocking channels, destabilizing structures, or any one of many other possible biological integrations. Upon identification of a new phenotype in a colony in the library, the effective BARP sequence can then be determined by isolating the DNA sequence from the cells of the colony exhibiting aberrant phenotypes, and then confirming biological effects in independently-transformed bacterial cells. This approach allows the use of BARPs to discover new regulators of bacterial growth and development, leading to identification of potential new high-value products.

Methods of Identifying BARPs in Prokaryotic Systems

In embodiments of the present disclosure of methods for identifying biologically active random peptides (BARPs) in bacterial systems or other prokaryotic systems, the method first includes providing a library of test nucleic acid sequences, where the test nucleic acid sequences encode a plurality of candidate BARPs. Each test nucleic acid sequence in the library includes nucleic acids encoding a start codon, a core random sequence of amino acids encoding a candidate BARP, and a stop codon. The length of the test nucleic acid sequence between the start and stop codons depends on the desired length of the encoded random sequence of amino acids (e.g., the candidate BARP), which may vary. In embodiments the test nucleic acid sequence between the start and stop codon includes nucleotides in multiples of 3, representing codons. In embodiments, the candidate BARP is from about 6 to about 20 amino acids long (e.g., the core random nucleic acid sequence is about 18 to about 60 nucleotides in length). In embodiments, the candidate BARP may include two flanking cysteine residues (i.e., the test nucleic acid sequence includes codons encoding a cysteine following the start codon and preceding the stop codon) to provide potential disulfide bonds, which may provide additional consistent structure and/or stability to the peptide. Thus, in embodiments with flanking cysteines the test nucleic acid sequence produces a small cyclized amino acid sequence.

In embodiments, the library of test nucleic acid sequences is made by generating a plurality of nucleic acid sequences, each encoding a core random sequence of amino acids. This can be done using methods known in the art, such as by using polymerase chain reaction (PCR) techniques to generate templates to produce random peptides when introduced via an expression system into a living cell/organism, such as a plant. In embodiments, a recombination cloning technique, such as the Gateway® cloning system, is used to generate an oligonucleotide library of test nucleic acid sequences. In embodiments, the test nucleic acid sequences described above are operatively linked between flanking primer sequences for recombination cloning (such as Gateway® sequences).

In some such embodiments, as illustrated in FIG. 1, the nucleic acid template used to generate PCR products includes, in sequence, a primer (e.g., a portion of the sequence where the first arrow is shown in FIG. 1), a start codon (e.g., ATG), a sequence of nucleotides encoding a random peptide sequence (represented by "NNN . . . " in FIG. 1), a stop codon (e.g., TAG, TAA, TGA), and the other flanking primer sequence. In embodiments, such as that illustrated in FIG. 1, the test nucleic acid sequence may include a spacer codon separating the core of the random peptide sequence from the start codon (e.g., the Ala codon "GCC" in SEQ ID NO: 1 or the Gly codon "GGC"). While any amino acid may be used as a spacer, Ala and Gly are least likely to interfere with the potential activity of a candidate peptide. In some embodiments, the test nucleic acid sequence may include nucleic acids encoding for two cysteines within or flanking the randomized core sequence. In embodiments, the encoded protein thereby includes two cysteines to provide sulfur-containing side chains, which have the ability to form disulfide bonds, which may add additional structure and internal stability to the random peptide by forming a cyclized peptide sequence.

In embodiments, with use of recombination cloning techniques, after building the template for PCR products as described above with the test nucleic acid flanked by the known recombination cloning sequences, the test sequences are amplified by PCR. Amplification by PCR can be done with primers corresponding to the known flanking sequence, which generates a reaction mix containing a plurality (e.g., hundreds, thousands, millions, etc.) of unique sequences, each coding for a different random peptide, each representing a candidate BARP. Each of these PCR products includes the flanking regions for cloning into recombination vectors as well as the start and stop sequences flanking the nucleotide sequence encoding the candidate BARP.

The methods of the present disclosure further include creating a library of recombination vectors from the library of test nucleic acid sequences. Each vector in the library includes a test nucleic acid sequence from the library operably linked to a nucleic acid sequence encoding a selectable marker to allow selection of cells/organisms successfully transformed with the recombination vector. In embodiments, the library of test nucleic acid sequences are cloned into recombination vectors that can be used for transforming the target bacteria (or other target prokaryotic organism) with the test nucleic acid sequences. In embodiments, recombination, or Gateway®, cloning techniques are used, in which the population of test nucleic acid sequences generated in the first step (e.g., with PCR methods) are moved to a shuttle vector or plasmid, such as those useful for bacterial cell transformation. In embodiments, the test nucleic acids can first be moved into an entry vector that can then be mobilized to other plasmids, such as bacterial vectors specific to the host organism. In embodiments the vectors are tailored to the host organism, such as by including ribosomal binding sites for transcription into gram-positive bacteria. The Gateway system, or other recombination cloning techniques, facilitate creation and amplification of the random test sequences, the transfer of the sequences between vectors, plasmids, and host organisms, and the isolation of the test sequences from an organism for sequencing after screening.

The library of test nucleic acid sequences generated as described above are cloned into the vectors to form a library of recombination vectors. Using these methods, each vector in the vector library includes a test nucleic acid from the library of test nucleic acid sequences. In embodiments, the recombination vectors also include a nucleic acid sequence encoding a selectable marker operably linked to the test nucleic acid. When expressed, the selectable marker produces a detectable signal (e.g., an observable phenotype, such as antibiotic resistance, color, fluorescence, etc.). This serves to identify bacterial cells and, later, plants and/or plant cells that include the test nucleic acid sequence encoding a candidate BARP (e.g., those that have been successfully transformed). In embodiments, the selectable marker can be, but is not limited to, antibiotic resistance, fluorescence, and the like. In embodiments, more than one (e.g., two or more, three or more, and the like) selectable markers can be operatively linked to the test nucleic acid. The use of more than one selectable markers allows for confirmation of transformation and/or for confirming the presence of the test nucleic acid at different stages of development or in different organisms (e.g., bacteria, etc.). For instance, in some embodiments, the test nucleic acid may be operatively linked to a nucleic acid encoding a peptide for antibiotic resistance as well as to a nucleic acid encoding a fluorescent peptide. In embodiments, the selectable marker is antibiotic resistance, and in some embodiments the test nucleic acid may be operatively linked to two or more nucleic acids encoding a peptide for antibiotic resistance (to different antibiotics) In embodiments the selectable marker can be, but is not limited to, kanamycin resistance, spectinomycin resistance, or both. In some embodiments the selective marker is tetracycline-inducible. In some embodiments, the selectable marker is fluorescence (such as, but not limited to, the jellyfish green fluorescent protein (GFP)). In embodiments, the recombination vectors include both antibiotic resistance and fluorescence selectable markers. Thus, for purposes of illustration, if the recombinant vectors including the test nucleic acid and both an antibiotic resistance and fluorescence selectable marker are used to transform bacterial cells, the cells can be screened by growth on plates containing antibiotic to screen for transformants including the antibiotic resistance selectable marker. For confirmation, fluorescence can also be tested. Additionally, if two antibiotic resistance genes are included as selectable markers, the cells can be screened by growth with both antibiotics or on two sets of plates (each with one of the two antibiotics), for additional confirmation of successful transformation of the host cell/organism. In embodiments, the vectors including the test nucleic acid sequences of the present disclosure may, in addition to primers, antibiotic resistance genes, and other functional sequences, may also include a targeting sequence directing expression of the proteins encoded by the nucleic acids in certain cells or organelles of the cell (e.g., the nucleus, endoplasmic reticulum, etc.)

The methods of the present disclosure further include transforming a population of bacterial cells (or other prokaryotic organism) with the library of recombination vectors to form a library of recombinant bacterial cells and colonies. In order to facilitate observation of new phenotypes, in embodiments, the population of bacteria is a phenotypically homogenous population of bacteria of the same species and strain. Using a phenotypically homogenous population of bacteria, where the individual cells/colonies share the same phenotypes (although some genetic differences may be present), makes it easier to identify the emergence of a new phenotype in an individual of the population, where such new phenotype can be associated with the candidate BARP encoded by the test nucleic acid sequence. In embodiments the population of host bacterial cells are also genetically identical, except for the transformation vector harboring the test nucleic acid sequence encoding the candidate BARP.

Methods for transforming bacteria (and other prokaryotic systems) using recombination vectors are known in the art. In embodiments, bacterial vectors are used to generate the library of vectors with test nucleic acid sequences. Then these bacterial vectors are transformed into a strain of bacteria. In embodiments, one strain of bacterial cells are transformed with the recombination vectors, and then the competent bacterial cells (e.g., as confirmed by the presence of the selectable marker) are isolated and screened. In embodiments, the plasmids/vectors are extracted from the competent bacterial cells and re-transformed into another population of bacterial cells (same or different strain) and screened for phenotypes in the second bacterial host.

In embodiments, the host bacterial cell is a gram-positive bacterial shuttle vector. In embodiments, the vector has features to facilitate transcription in the host bacteria, such as ribosomal binding sites. In embodiments the shuttle vector is used to transform a first strain of bacteria (e.g., *E. coli*), and, after positive screening (e.g., on antibiotic resistant media), the plasmids can be extracted from competent transformants and applied for transformation of a different bacterial strain (e.g., *Streptococcus mutans, Staphylococcus aureus*, etc.). In embodiments, the vector is an *E. coli*/gram-positive bacterial shuttle vector, such as, but not limited to pDL278. In embodiments, the vector is tailored for transformation of the host organism, such as by including specific restriction enzyme sites specific cassette sequences, and the like. In embodiments, a destination vector pDL278GW, designed as described in the examples below, is used for transformation of *S. mutans* bacterial strains. In embodiments, bacterial cells containing the vectors (and, hence the test nucleic acid encoding the candidate BARP) can be identified by the presence of the signal produced by the selectable marker (e.g., growth on antibiotic selection media, fluorescence, etc.).

In embodiments, the competent bacterial cells are used to produce a library of colonies each colony containing a test nucleic acid sequence encoding a candidate BARP. Bacterial cells that have been successfully transformed are then identified by the presence of the signal produced by the selectable marker (e.g., antibiotic resistance, fluorescence, combinations of these, and the like) in the bacterial colonies.

Using the above methods, a library of transformed bacterial cells can be generated, where each bacterial cell/colony includes a recombination vector from the library and thus a candidate BARP. While it will be recognized that, at each stage above involving the creation of a "library" (of test nucleic acids, of recombination vectors, of bacterial cells, etc.), it is intended that each individual of the library include a different test nucleic acid encoding a different candidate BARP, some chance duplication could occur, or a host cell could, by chance, contain two recombination vectors. Thus, the terms "each" and "different" in this disclosure and the accompanying claims are not meant to be absolute, but merely to convey that, in general, each member of the library corresponds to a different candidate BARP, with allowances for some natural duplication. Furthermore, it will be understood that, in order to screen for new phenotypes (associated with a candidate BARP) in a bacterial cell/colony, the bacteria in the bacterial library will typically all be of the same species/strain. This is to ensure that any variation in phenotype between cells is associated with and attributable to the presence of the BARP rather than due to another genetic difference between cells. Various bacterial species can be used in the methods of the present disclosure, but for purposes of illustration, the examples provided utilized *Streptococcus mutans*. The bacterial strains can be screened for phenotypical differences, such as colony morphology, lac Z activity, colony growth in various pH conditions, autolysis, and the like. In embodiments, the bacterial strain used in methods of the present disclosure is *S. mutans* having lacZ activity, in order to assess changes in lacZ activity when grown in the presence of X gal (determined by intensity of blue color produced by the colonies). In embodiments, the strain is *S. mutans* UA159$_{Pcom\ X:lacZ}$).

Other bacterial systems can also be used for all stages, particularly for further confirmation of an observed phenotype. For instance, BARPs identified in the methods of the present disclosure in *S. mutans* can then be transformed into other bacterial systems to determine if the BARP has similar activity and phenotypic effect in other bacterial species/strains. In embodiments, other plant systems for use in the methods and systems of the present disclosure include, but are not limited to, *Staphylococcus aureus*.

As described above, the identified BARP can then be isolated from the bacterial cell with the new phenotype using known methods, and the sequence of the BARP can be determined. The putative activity of the BARP can be confirmed by transforming new bacterial cells with the BARP to observe for recapitulation of the observed phenotype in the newly transformed cells. This offers further evidence that the observed phenotype is caused by the BARP. In embodiments, the identified BARP can be further tested in a different strain or species of bacteria to determine if the BARP has activity (similar or different activity) in other bacterial strains/species. Additional details regarding embodiments of methods of making libraries of recombinant vectors are described in the examples below.

BARP Prokaryotic Libraries

Embodiments of the present disclosure also include recombinant prokaryotic/bacterial libraries made according to the methods of the disclosure described above. In embodiments, a library of transformed bacterial cells of the present disclosure includes a plurality of bacterial cells/colonies (where the bacteria were phenotypically homogenous prior to transformation and/or where the bacterial cells had the same original genotype), each cell/colony including a different recombination vector. As described above, each recombination vector in each cell/colony in the library includes a test nucleic acid sequence encoding a start codon, a random sequence of amino acids, and a stop codon as well as a nucleic acid sequence encoding a selectable marker operably linked to the test nucleic acid sequence. The test nucleic acid sequence in each vector, and thus in each transformed cell/colony, encodes a different random sequence of amino acids (with exception for a small potential number of duplicates, as mentioned above).

According to methods of the present disclosure, after transformation of the bacterial cells and generation of a bacterial library, the library of recombinant bacteria is then plated and screened for the occurrence of a new phenotype (e.g., a phenotype that is discernible from a wild type bacterial cell or colony). With the methods of the present disclosure, the bacterial colony growth can be observed, and thus screened, throughout the full stages of development. When a new phenotype occurs in one of the recombinant bacterial colonies, this indicates that the candidate BARP may be responsible for the new phenotype. In other words, the presence of a new phenotype indicates that the expressed candidate BARP may be interfering with or in some way modifying a biological process of the bacterial cells in the colony to directly or indirectly produce the new phenotype.

Examples of new phenotypes that may occur in the methods of the present disclosure may manifest as a general defect, a discrete defect, or both. In embodiments, the new phenotype can be a different colony morphology, a change in growth rate, a change in growth under certain environmental conditions (e.g., pH, selective media, etc.), the reduction or loss of B-gal activity (as indicated by a loss of blue color when grown on X-gal containing medium), and the like.

Upon detection of a new phenotype in a colony from the library, the DNA is extracted from the cells of the colony exhibiting the new phenotype, and the sequence of the candidate BARP is determined. This can be done by known sequencing methods. In embodiments, the sequences can be isolated by PCR using the same primers used in the construction of the test nucleic acid library (e.g., Gateway sequences or other recombination cloning primers), followed by DNA sequencing.

Since it is possible that the new phenotype may be the result of some other random, naturally occurring event or T-DNA insertion, additional tests may be done before positively attributing the new phenotype to the candidate BARP. Thus, in embodiments, the association of the candidate BARP with the new phenotype is confirmed by additional testing. To verify that the candidate BARP is associated with the new phenotype, after determining the sequence of the candidate BARP, additional bacterial cells are transformed with the nucleic acid sequence encoding the BARP (e.g., according to the methods described above or other transformation methods known in the art). If the colonies of the newly transformed cells also display the new phenotype, this recapitulation of phenotype indicates that the candidate BARP is a BARP responsible for the new phenotype.

While unlimited strains of bacteria can be used with the methods described above, in embodiments, the bacteria is selected from strains of *E. coli, S. mutans, S. aureus*, and others. Embodiments described in the Examples below illustrate the methods of the present disclosure using strains of *S. mutans*, which have thus far resulted in the identification of several new BARPs. This confirms that the method can be successfully employed to generate libraries of candidate BARPs and to identify new biologically active peptides.

Not only do the methods of the present disclosure permit identification of novel biologically-active peptides, these newly identified peptides can be utilized in the plant industry. For instance, depending on the resulting phenotype, such peptides can be installed or applied as commercial growth regulators, probiotics, antibiotics, and the like.

Bacterial BARPS

Embodiments of the present disclosure also include identified bacterial BARPs that induce a specific phenotype in bacterial colonies. In embodiments, bacterial BARPS were identified in *S. mutans* strain UA159$_{Pcomx::lacZ}$. Although numerous BARPs have been identified, the following table lists representative BARP sequences that produce confirmed phenotypes relating to colony morphology and lacZ competency (two sequences, 6AA-6 and RBS6AA-11 that produced normal phenotypes with respect to colony morphology and competency are listed as well and were used as controls in experiments described in the Example below). In the table, sequences are identified by SEQ ID NO. The nucleotide and peptide sequences associated with each SEQ ID NO are listed below and in the accompanying sequence listing. Note: BARPs with identical sequences are listed together.

TABLE 1

| BARP sequence Name | SEQ ID NO (nucleotide sequence identifier is listed first, peptide sequence second) | Phenotype: colony morphology | Phenotype: competency |
|---|---|---|---|
| 6AA-6 | SEQ ID NO: 2, 13 | Normal morphology: small and rough. | Normal competency: blue color |
| RBS6AA-11 | SEQ ID NO: 3, 14 | Normal morphology: small and rough. | Normal competency: blue color |
| 12AA-1,-3,-4 (same sequence) | SEQ ID NO: 4, 15 | | Less blue |
| 12AA-2,-5,-7,-10 (same sequence) | SEQ ID NO: 5, 16 | Mucoid | |
| 12AA-6 | SEQ ID NO: 6, 17 | Mucoid | |
| 12AA-11 | SEQ ID NO: 7, 18 | Mucoid | |
| RBS6AA-1 | SEQ ID NO: 8, 19 | Mucoid | |
| RBS6AA-10 | SEQ ID NO: 9, 20 | Mucoid | |
| RBS6AA-12 | SEQ ID NO: 10 (no SEQ ID for corresponding peptide due to likely early stop of translation resulting in shortened peptide | Mucoid | |
| RBS12AA-5 | SEQ ID NO: 11, 21 | Mucoid | Less blue |
| RBS12AA-9 | SEQ ID NO: 12, 22 | Mucoid | Less blue |

Thus, in embodiments, the present disclosure also provides isolated BARPs encoded by a nucleic acid sequence having a sequence selected from: SEQ ID NOs: 4-12. Embodiments of the present disclosure also include isolated BARPs having a peptides sequence selected from: SEQ ID NOs: 15-22. The present disclosure also provides recombination vectors including a nucleic acid sequence selected from SEQ ID NOs: 4-12 and encoding a BARP having a peptide sequence selected from: SEQ ID NOs: 15-22. In embodiments, the BARP is operably linked with a promoter sequence to drive expression of the BARP in a host bacterial cell. In embodiments, the BARP is operably linked with a selectable marker for identification of cells/colonies expressing the BARP, such as antibiotic resistance, tetracycline induced, fluorescence, and the like.

Embodiments also include methods of conferring a desired phenotype in a bacterial cell or colony by transforming the plant with a specific BARP capable of inducing the phenotype, or otherwise introgressing the BARP into the bacterial genome. Embodiments include methods of providing bacteria having mucoid colony phenotype by transforming the bacteria with a vector including nucleic acid sequences SEQ ID NOs: 5-12, encoding a BARP having peptides sequence selected from: SEQ ID NO: 16-22. Embodiments include methods of providing bacteria having a loss of lacZ competency by transforming the bacterial cell with a nucleic acid sequence encoding a BARP having a peptide sequence selected from: SEQ ID NOs: 15, 21, and 22 (nucleic acid sequences SEQ ID NOs: 4, 11, and 12). Embodiments include methods of providing bacteria having a phenotype characterized by mucoid colonies and a less blue (loss of lacZ competency phenotype) by transforming the bacteria with a nucleotide sequence encoding a BARP having SEQ ID NO: 21 or 22 (nucleic acid sequences SEQ ID NOs: 11 and 12, respectively). Although not listed in Table 1 above, Example 1 below demonstrates that some of the identified BARPS (peptide 12AA-2, -5, -7, and -10, SEQ ID NO: 16, (four independent transformants) encoded by nucleic SEQ ID NO: 5) also have a phenotype related to prolonged growth from a failure to enter autolysis (as compared to control strain 6AA-6) when grown at neutral pH. Thus, in embodiments, the present disclosure provides methods of providing bacteria having prolonged growth at neutral pH by transforming the bacteria with a nucleotide sequence encoding a BARP having SEQ ID NO: 16 (nucleic acid sequence SEQ ID NO: 5). In embodiments, the new observed phenotypes are associated with desired phenotypes for possible products. For instance, the mucoid phenotype is associated with less virulence. In the case of *S. mutans*, mucoid colony morphology is associated with a loss or decrease in cariogenicity. Thus such mutants could be useful for reducing cariogenicity (e.g., as a probiotic).

In embodiments of the above methods, the bacteria is any bacterial species/strain where the phenotype associated with the BARP is desired. In embodiments, the bacterial organism is *S. mutans*. In embodiments, the bacterial cell is transformed with a vector including the target BARP operably linked to a promoter sequence and/or a selective marker. The methods, systems, and BARPs of the present disclosure provide new ways to modify bacterial growth and development and introduce new and useful bacterial phenotypes.

The methods of the present disclosure provide the ability to rapidly identify new compounds for use in regulating biological processes with molecules that likely have outstanding safety profiles for the environment and human health. This offers benefits of reduced costs, reduced time for identification and testing of such compounds, and improved safety. The methods of the present disclosure described above can be applied to other transformable organisms, and could extend to peptide-based applications in other prokaryotic organisms, animals and microorganisms such as fungi, and the like.

Additional details regarding the methods and compositions of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. Publications are incorporated by reference only where indicated by notation in the text, such references are incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure Example 1

In the example below, the methods of the present disclosure were used to generate a library of test nucleic acids encoding a plurality of candidate BARPs, each having a core 6 amino acid random peptide sequence flanked by two cysteine residues. The sequences were also flanked by start and stop codons and Gateway® sequences, such as illustrated in FIG. 1. PCR was used with primers corresponding to the known Gateway flanking sequences to generate the test nucleic acid library. The oligonucleotides were then cloned into bacterial vectors including genes for antibiotic resistance to create a recombination vector library. The vectors were then used to transform Streptococcus mutans. The transformed cells were plated on selective media and colony growth was for new phenotypes. Several new phenotypes emerged, DNA was extracted from the colonies displaying new phenotypes, and the sequence of the candidate BARP from the cells was determined. The procedures and results are described in detail below.

Materials & Methods

Construction of Random Small Peptide Libraries

DNA oligos encoding peptides: MAC C (referred as 6AA, six random amino acid peptides) or MGC C (referred as 12AA, twelve random amino acid peptides), flanked with partial attB1 and attB2 sequences, were amplified using attB universal adaptor primers. In order to ensure the correct transcription in gram-positive bacteria, ribosomal binding sites with 8 bps spacer in front of the translational codon were also introduced into DNA oligos named RBS6AA and RBS12AA. PCR products were cloned into the entry vector pDONR222 through BP reaction following the manufacture's procedure (Cat. #11789020, ThermoFisher Scientific). Plasmids were extracted from bulked bacterial transformants and referred as random small peptide entry libraries.

The vector of pDL278 is an E. Coli/Gram-positive Bacterial Shuttle Vector (LeBlanc et al., 1992). The cutting sites of restriction enzymes KpnI and SacI were introduced into ends of attR1-ccdB-attR2 cassette sequences through PCR amplification, respectively. Both attR1-ccdB-attR2 cassette and pDL278 vector were digested with KpnI and SacI, and ligated with T4 DNA ligase. The resulted construct was referred as the destination vector pDL278GW. All four random small peptide libraries were migrated into pDL278GW vector through LR reactions following the manufacture's procedure (Cat. #11791100, ThermoFisher Scientific), respectively. Plasmids were extracted from bulked bacterial transformants and applied for the transformation of S. mutans. The vectors also included genes for spectinomycin and kanamycin resistance as selective markers to screen for successful transformants.

Transformation and Screening of S. mutans Strain Transformed with Random Peptide Libraries S. mutans strain $P_{comX::lacZ}$ was incubated in Brain-heart infusion (BHI) broth at 37° C. with 5% $CO_2$ overnight. For one transformation, 1/50 dilution of overnight culture with 1 ml fresh BHI broth, 1 µg peptide library plasmids and 10 µl CSP18 (1 µM) were combined and incubated for 3-4 hours. Transformants were grown on BHI agar plates containing 1 mg/ml spectinomycin and 1 mg/ml kanamycin antibiotics for 2 days. All bacterial colonies from each library were collected and bulked for a strain stock. A 10"7 dilution of strain stock was grown on TYL induction medium (tryptone, yeast extracts and lactose) supplied with X-gal for 2 days. Mucoid and/or less blue colonies were chosen for the further confirmation.

Plasmid Extraction, Sequencing and Retransformation into S. mutans Strain

Colonies with reproducible phenotypes were incubated in 10 ml BHI broth supplied with 1 mg/ml spectinomycin and 1 mg/ml kanamycin antibiotics, and resultant bacteria were used for plasmid extraction following the protocol described previously (Xie et al., 2013, which is hereby incorporated by reference herein). Due to the low yield of plasmids extracted from S. mutans, peptide fragments were amplified using M13F and M13R primers, and these PCR products were sequenced. Meanwhile, plasmids were reintroduced into the $P_{comX::lacZ}$ strain to test whether phenotypes are identical to that observed from the original screening.

S. mutans Growth Measurement and Acidic Stress Assay

To test whether S. mutans growth is affected by the introduction of small peptide sequences, overnight cultures of each bacterial isolate were diluted for 100 times with prewarmed BHI medium and grown at 37° C. in a 5% $CO_2$ atmosphere to reach $OD_{600}$ 0.5. The cells were then diluted with fresh BHI medium (PH 7.0) or PH 5.5 for acidic stress assay and distributed into 96-well microplate with tree replicates. Each well of cultures was covered by one drop of sterile mineral oil to achieve anaerobic growth conditions. The plates were incubated for 48 hours in an aerobic chamber, and bacterial growth was monitored and recorded using a Bioscreen C lab system (Helsinki, Finland).

Results & Discussion
S. mutans Screened with a Random Small Peptide Collection Identifies Peptides that Exhibit Variation in Morphology and Alteration of Competency.

Figure 3A:
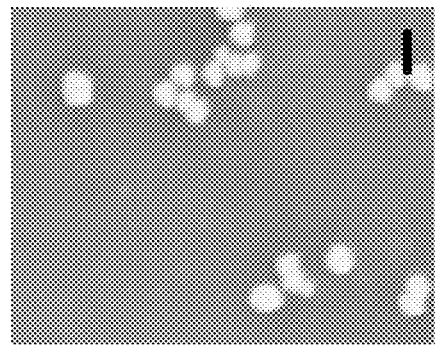
FIGS. 3A-3D are digital images illustrating the effect of some of the tested BARPs on lacZ activity of *S. mutans* UA159 PcomX::lacZ.

Four small random peptide libraries were constructed (6AA, 12AA, RBS6AA and RBS12AA) in the shuttle vector pDL278GW vector and expressed in S. mutans strain $P_{comX::lacZ}$ to identify candidate peptides affecting the virulence of S. mutans. Colonies each expressing a random, cyclical peptide were assessed for morphology and color. The typical, wild-type S. mutans colony is rough, heaped, irregular and 0.5-2.0 mm in diameter (FIG. 2A), while abnormal colonies are mucoid and large (FIGS. 2B-2L). The mucoid colony morphology is likely associated with the decrease of cariogenicity (Okahashi et al., 1984). The gene ComX encodes a sigma factor that is required for the late competence gene expression and transformation (Lee and Morrison, 1999). A reporter system using LacZ gene driven by ComX promoter was introduced into S. mutans to indicate changes in competency (Son et al., 2012). Normal bacterial colonies exhibit a blue color when they grow on medium supplied with X-gal (FIG. 3A), while abnormal colonies are white or less blue.

Figure 3B:
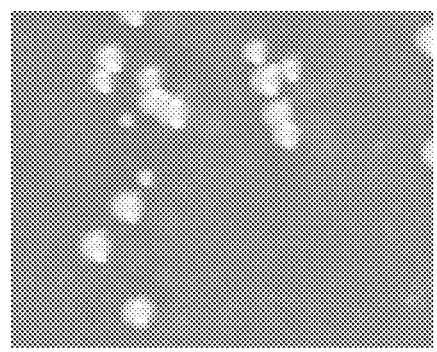
Figure 3C:
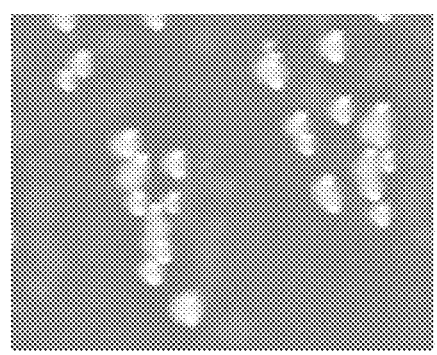
Figure 3D:
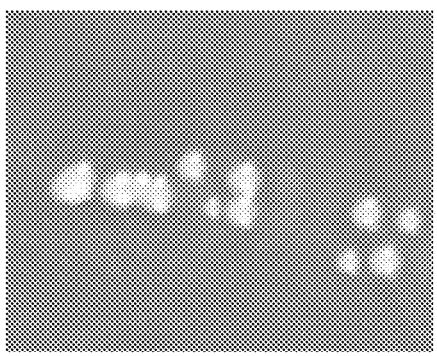

Four libraries were introduced into this strain, and 12 abnormal colonies were identified in the resulting transformants. Characterized defects were divided into three categories: mucoid, decreased LacZ activity (less blue) and mucoid plus less blue. For mucoid and mucoid plus less blue colonies, colonies were streaked and grown on BHI medium to analyze colony morphology. Eleven of the initial transformants exhibited a reproducible mucoid phenotype (FIGS. 2B-2L, Table 2). For less blue and mucoid plus less blue colonies, colonies were re-streaked and grown on YPL medium with X-gal to analyze the colony color. Only three produced the less blue phenotype (FIGS. 3B-D, table 2). All these data suggest that the installed peptide sequence has the capacity to affect the virulence of S. mutans.

Multiple Peptide Sequences Affect Colony Morphology and Competency in S. mutans.

Discrete peptide sequences were identified by sequencing PCR products amplified from plasmids recovered from mucoid or less-blue S. mutans transformants. The three colonies exhibiting a less-blue phenotype (12AA-1, 12AA-3 and 12AA-4) contained identical DNA sequences. Four out of eleven mucoid colonies (12AA-2, 12AA-5, 12AA-7 and 12AA-10) also contained identical DNA sequences. The rest of the seven mucoid colonies contain different sequences (see Table 1, above and sequence listing, below).

To test if the mucoid morphology or less blue color of S. mutans colonies is due to the inserted plasmid sequence and not some secondary mutation, the isolated sequences were re-transformed back to S. mutans strain $P_{comX::lacZ}$. FIGS. 5A-5H show that control sequence 6AA-6 demonstrated the normal, rough and small colony morphology while re-transformants (except RBS12AA-5) exhibited mucoid colony morphology, which is identical to the original observation (FIGS. 5B-H, table 2).

One Peptide Sequence LED to Defective Autolysis in S. mutans

Autolysis that is utilized by certain strains to facilitate the survival of populations of organisms, and is essential for virulence and biofilm formation of S. mutans (Ahn et al., 2007; Ahn et al., 2010). Acid tolerance response (ATR) is one mechanism for S. mutans to survive in an acidic environment with pH below 3.0 (Burne, 1998). In order to test whether S. mutans strains transformed with small peptides have defects on autolysis or ATR, the 14 original bacterial isolates with abnormal phenotypes and two controls (6AA-6 and RBS6AA-11) were grown in BHI broth at PH7.0 (neutral) or PH 5.5 (acidic). Growth was monitored for 48 hours. In pH neutral conditions, four S. mutans strains (12AA-2, -5, -7 and -10) transformed with same peptide sequence all exhibited prolonged growth compared with the control strain transformed with the peptide 6AA-6, suggesting defects in autolysis (FIG. 4A). However, all strains grew with similar kinetics when the BHI medium was acidic (FIG. 4B). The strain transformed with the peptide 12AA-5 had a longer lag time for its growth compared with the control strain and other strains containing the same peptide sequences.

Example 2

Randomized peptide libraries were made as described above in the vector pDONR222 and were transferred to the gram-positive bacterial vector pTX15. This vector allows the sequence to be transferred to gram-positive bacteria and expressed in a tetracycline-inducible manner. Such libraries can then inserted into pathogenic bacteria and screened for normal growth under non-induced conditions, and then for slowed growth under tetracycline induction.

In the present Example, the libraries were transferred to the pTX15 vector after it was modified to accept Gateway sequence using known methods. These modified libraries also included a ribosome binding site to ensure efficient translation. The libraries were amplified and purified from E. coli strain DH5α, and then added to competent gram-positive competent Staphylococcus aureus using electroporation. The same vectors were also added to S. mutans using pheromone-mediated transformation. Such methods are known in the art.

Example 3

The prokaryotic libraries prepared as described in Example 3 in Staphylococcus aureus and S. mutans are grown under tetracycline induction and examined for growth phenotypes.

In S. aureus the bacteria contain the RNAIII promoter driving GFP, so bacterial colonies can be screened for defects in quorum sensing leading to virulence.

Streptococcus mutans features a substantial number of mutants that exhibit clear colony morphologies on media containing sucrose. The S. mutans libraries are plated on MS or BH1 agar containing sucrose. BARP activity is evidenced by altered colony morphology from changes in cellular shape or sucrose-chain length.

Selection of S. mutans and S. aureus colonies exhibiting defects in colony morphology or growth when the BARP sequence is induced will reveal sequences that can then be re-transformed into new cells to examine for recapitulation of the alteration of colony morphology. Such evidence would then lead to more complex examinations of molecular mechanisms, using genetic tools and biochemical interaction studies.

TABLE 2

Summary of phenotypes of S. mutans strains transformed with small peptides

| Name | Morphology | | |
|---|---|---|---|
| | Original | 2nd Streak | Retranformatoin |
| 12AA-1 | Less blue | Less blue | |
| 12AA-2 | Mucoid | Mucoid | Mucoid |
| 12AA-3 | Less blue | Less blue | |
| 12AA-4 | Less blue | Less blue | |
| 12AA-5 | Mucoid | Mucoid | Mucoid |
| 12AA-6 | Mucoid | Mucoid | Mucoid |
| 12AA-7 | Mucoid | Mucoid | Mucoid |
| 12AA-10 | Mucoid | Mucoid | Mucoid |
| 12AA-11 | Mucoid | Mucoid | Mucoid |
| RBS6AA-1 | Mucoid | Mucoid | Mucoid |
| RBS6AA-10 | Mucoid | Mucoid | Mucoid |
| RBS6AA-12 | Mucoid | Mucoid | Mucoid |
| RBS12AA-5 | Less blue and Mucoid | Mucoid | Rough and blue |
| RBS12AA-9 | Less blue and Mucoid | Mucoid | Mucoid |
| 6AA-6 | Rough and blue | Rough and blue | Rough and blue |
| RBS6AA-11 | Rough and blue | Rough and blue | Rough and blue |

Sequences:
SEQ ID NO: 1 (artificial nucleotide sequence of a test nucleic acid encoding a random peptides sequence for a candidate BARP, where "n" is any nucleotide. Double underlining indicates start codons and single underlining indicates stop codons, and bold indicates cysteine codons)

ATGGCCTGTNNNNNNNNNNNNNNNNNNNTGTTAG

SEQ ID NO: 2 (nucleotide sequence of control BARP 6AA-6 associated with normal growth and competency)

ATGGCCTGTGTGCGGGTGTGGATGGGGTGTTAG

SEQ ID NO: 3 (nucleotide sequence of control BARP RBS6AA-11 associated with normal growth and competency)

ATGGCCTGTTACACCGGTCATGCTACTTGTTAG

SEQ ID NO: 4 (nucleotide sequence of BARP 12AA-1, -3, and -4 associated with less blue phenotype (e.g., less competency); note early stop codon "TAG" at nucleotides 43-45 likely resulting in a slightly truncated peptide)

ATGGGCTGTTTTCAACGAACCGGTTGTCTTGGCACGGTGCGATAGTGTTAG

SEQ ID NO: 5 (nucleotide sequence of BARP 12AA-2, -5, -7, and -10 associated with mucoid growth and defects in autolysis)

ATGGGCTGTGTGGCAGGGCCCTGCGGCCTGACGGCGCGTAACTTTTGTTAG

SEQ ID NO: 6 (nucleotide sequence of BARP 12AA-6 associated with mucoid growth and normal competency)

ATGGGCTGTTTCCAAAGTGTTCAGCAGCTTCCTCTCGTTCTCAAATGTTAG

SEQ ID NO: 7 (nucleotide sequence of BARP 12AA-11 associated with mucoid growth and normal competency; note early stop codon "TGA" at nucleotides 42-44 likely resulting in a truncated peptide)

ATGGGCTGTTATGGGTCTTTTACACTACGTTTCATTTGAAATGATTGTTAG

SEQ ID NO: 8 (nucleotide sequence of BARP RBS6AA-1 associated with mucoid growth and normal competency)

ATGGCCTGTATTTTATGCCATCAATTATGTTAG

SEQ ID NO: 9 (nucleotide sequence of BARP RBS6AA-10 associated with mucoid growth and normal competency)

ATGGCCTGTGCCCCTGTTGTTAATAAGTGTTAG

SEQ ID NO: 10 (nucleotide sequence of BARP RBS6AA-12 associated with mucoid growth and normal competency; note early stop codon "TGA" at nucleotides 10-12 likely resulting in a truncated peptide, MAC, which is not given a SEQ ID NO due to the shortened length)

ATGGCCTGTTGACAATTTGTCCTTAAATGTTAG

SEQ ID NO: 11 (nucleotide sequence of BARP RBS12AA-5 associated with mucoid growth and less blue phenotype)

ATGGGCTGTTTTATTGGGTTCTTGTTCCCACAGTATGAACTTGTTTGTTAG

SEQ ID NO: 12 (nucleotide sequence of BARP RBS12AA-9 associated with mucoid growth and less blue phenotype; note early stop codon "TAA" at nucleotides 22-24 likely resulting in a truncated peptide)

ATGGGCTGTCACACTTTTATTTAACCGGCTCAGTCTTGCTGACTATGTTAG

SEQ ID NO: 13 (peptide sequence of 6AA-6, SEQ ID NO: 2)

MACVRVWMGC

SEQ ID NO: 14 (peptide sequence of RBS6AA-11, SEQ ID NO: 3)

MACYTGHATC

SEQ ID NO: 15 (peptide sequence of 12AA-1, -3, and -4, SEQ ID NO: 4; NOTE: the stop codon "TAG" at nucleotides 43-45 of SEQ ID NO: 4 likely results in early termination, producing SEQ ID NO: 18, below)

MGCFQRTGCLGTVR

SEQ ID NO: 16 (peptide sequence of 12AA-2, -5, -7, and -10, SEQ ID NO: 5)

MGCVAGPCGLTARNFC

SEQ ID NO: 17 (peptide sequence of 12AA-6, SEQ ID NO: 6)

MGCFQSVQQLPLVLKC

SEQ ID NO: 18 (peptide sequence of 12AA-11, SEQ ID NO: 7; NOTE: the stop codon "TGA" at nucleotides 42-44 of SEQ ID NO: 7 likely results in early termination, producing SEQ ID NO: 18, below)

MGCYGSFTLRFI

SEQ ID NO: 19 (peptide sequence of RBS6AA-1, SEQ ID NO: 8)

MACILCHQLC

SEQ ID NO: 20 (peptide sequence of RBS6AA-10, SEQ ID NO: 9)

MACAPVVNKC

NOTE: for the peptide sequence of RBS6AA-12 encoded by nucleotide sequence SEQ ID NO: 10, the stop codon "tga" occurring at nucleotides 10-12 of SEQ ID NO: 10 likely results in early termination, producing the 3-amino-acid sequence: MAC, which due to the short length is not assigned a SEQ ID NO.

SEQ ID NO: 21 (peptide sequence of RBS12AA-5, SEQ ID NO: 11)

MGCFIGFLFPQYELVC

SEQ ID NO: 22 (peptide sequence of RBS12AA-9, SEQ ID NO: 12; note, the stop codon "TAA" at nucleotides 22-24 of SEQ ID NO: 12 likely results in early termination, producing the shorter peptide sequence of SEQ ID NO: 22, below)

MGCHTFI

REFERENCES

Ahn, S. J., Wen, Z. T., and Burne, R. A. (2007). Effects of oxygen on virulence traits of *Streptococcus mutans*. J Bacteriol 189, 8519-8527.

Ahn, S. J., Rice, K. C., Oleas, J., Bayles, K. W., and Burne, R. A. (2010). The *Streptococcus mutans* Cid and Lrg systems modulate virulence traits in response to multiple environmental signals. Microbiology 156, 3136-3147.

Burne, R. A. (1998). Oral streptococci . . . products of their environment. J Dent Res 77, 445-452.

LeBlanc, D. J., Lee, L. N., and Abu-Al-Jaibat, A. (1992). Molecular, genetic, and functional analysis of the basic replicon of pVA380-1, a plasmid of oral streptococcal origin. Plasmid 28, 130-145.

Lee, M. S., and Morrison, D. A. (1999). Identification of a new regulator in *Streptococcus pneumoniae* linking quorum sensing to competence for genetic transformation. J Bacteriol 181, 5004-5016.

Okahashi, N., Asakawa, H., Koga, T., Masuda, N., and Hamada, S. (1984). Clinical isolates of *Streptococcus mutans* serotype c with altered colony morphology due to fructan synthesis. Infect Immun 44, 617-622.

Son, M., Ahn, S. J., Guo, Q., Burne, R. A., and Hagen, S. J. (2012). Microfluidic study of competence regulation in *Streptococcus mutans*: environmental inputs modulate bimodal and unimodal expression of comX. Mol Microbiol 86, 258-272.

Xie, Z., Qi, F., and Merritt, J. (2013). Cloning-independent plasmid construction for genetic studies in streptococci. J Microbiol Methods 94, 77-82.

Spring D R (2005) Chemical genomics: Small molecules offer big insights. Chem Soc Rev 34:472-482.

Higashigmia T, et al. (1988) Mastoparan, a peptide toxin from wasp venom, mimics receptors by activating GTP-binding regulatory proteins. J. Biol. Chem. 263, 6491-6494.

Abdiche, Y., et al., 2008. Determining kinetics and affinities of protein interactions using a parallel real-time label-free biosensor, the Octet. Anal. Biochem. 377: 209-217.

Alonso, J. M., et al., 2003. Genome-wide insertional mutagenesis of *Arabidopsis thaliana*. Science 301: 653-657.

Yamada, K., et al., 2003. Empirical analysis of transcriptional activity in the *Arabidopsis* genome. Science 302: 842-846.

Estevez, J. M. and C. Somerville. 2006. FlAsH-based live-cell fluorescent imaging of synthetic peptides expressed in *Arabidopsis* and tobacco. BioTechniques 41: 569-70, 572.

The invention claimed is:

1. A method for identifying biologically active random peptides (BARPs) in bacterial cells, the method comprising:

providing a library of test nucleic acid sequences, the library comprising a plurality of different test nucleic acid sequences encoding a plurality of candidate BARPs, wherein each test nucleic acid sequence consists of nucleic acids encoding, in the following order a start codon, a spacer codon selected from alanine or glycine, a first cystine residue, a random sequence of 6-20 amino acids representing a candidate BARP, a second cysteine residue, such that the first and second cysteine residues flank the random sequence of amino acids, and a stop codon, and wherein each test nucleic acid sequence in the library is flanked by recombinatorial cloning primer sequences;

creating a library of recombination vectors from the library of test nucleic acid sequences, wherein each vector comprises a test nucleic acid sequence from the library and a nucleic acid sequence encoding a selectable marker operably linked to the test nucleic acid sequence;

transforming a plurality of phenotypically homogenous bacterial cells with the library of recombination vectors, wherein the bacterial cells are selected from the group consisting of: *Escherichia coli*, *Streptococcus mutans*, and *Staphylococcus aureus*;

screening the bacterial cells for the presence of the selectable marker, selecting bacterial cells with the selectable marker to produce a library of recombinant bacterial cells, wherein each recombinant bacterial cell comprises a recombination vector from the library, wherein identification of the selectable marker indicates expression of a candidate BARP by the recombinant bacterial cell;

screening the library of recombinant bacterial cells throughout development for the occurrence of a new phenotype, wherein the new phenotype is discernible from the phenotype of a corresponding wild type bacterial cell without the candidate BARP and wherein the presence of the new phenotype indicates the candidate BARP is responsible for the new phenotype; and, upon observance of a new phenotype, determining the sequence of the candidate BARP from the recombinant bacterial cells exhibiting the new phenotype.

2. The method of claim 1, further comprising:

verifying the new phenotype associated with the candidate BARP by independently transforming additional bacterial cells with a vector encoding the candidate BARP; and screening for the presence of the new phenotype, wherein the presence of the new phenotype in the new transformed bacterial cell indicates that the candidate BARP is responsible for the new phenotype.

3. The method of claim 1, wherein the random sequence of amino acids is 6 amino acids in length and wherein each test nucleic acid in the library consists of SEQ ID NO: 1, wherein "n" represents any nucleotide, and wherein each "n" for each test nucleic acid sequence in the library is independently selected.

4. The method of claim 1, wherein the random sequence of amino acids is 12 amino acids in length.

5. The method of claim 1, further comprising, testing the activity of the candidate BARP in a second bacterial species by independently transforming a plurality of phenotypically homogenous cells of a second species of bacteria with a vector encoding the candidate BARP, and screening for the presence of the new phenotype, wherein the presence of the new phenotype in the transformed bacterial cells of the second plant species indicates that the candidate BARP is responsible for the new phenotype and that the candidate BARP is active in a second bacterial species.

6. The method of claim 1, wherein the selectable marker is selected from the group consisting of: antibiotic resistance, fluorescence, tetracycline-inductance, and a combination of these.

7. The method of claim 1, wherein the recombination vector encodes two or more different selectable markers, wherein the nucleic acid sequence encoding each selectable marker is operably linked to the test nucleic acid sequence.

8. The method of claim 1, wherein at least one of the selectable markers is antibiotic resistance.

9. The method of claim 1, wherein at least one of the selectable markers is fluorescence.

10. The method of claim 7, wherein the two or more selectable markers comprise a nucleic acid sequence encoding a kanamycin resistance gene and a nucleic acid sequence encoding a spectinomycin resistance gene.

11. The method of claim 1, wherein the plurality of phenotypically homogenous bacterial cells comprise *Streptococcus mutans*.

12. The method of claim 1, wherein recombination cloning methods are used to generate the library of recombination vectors.

* * * * *

SEQUENCE LISTING

```
<160> NUMBER OF SEQ ID NOS: 22

<210> SEQ ID NO 1
<211> LENGTH: 33
<212> TYPE: DNA
<213> ORGANISM: Artificial Sequence
<220> FEATURE:
<223> OTHER INFORMATION: chemically synthesized nucleotide sequence of
      a test nucleic acid encoding a random peptide sequence for a
      candidate BARP
<220> FEATURE:
<221> NAME/KEY: misc_feature
<222> LOCATION: (10)..(27)
<223> OTHER INFORMATION: n is any nucleotide

<400> SEQUENCE: 1
atggcctgtn nnnnnnnnn nnnnnnntgt tag                                   33

<210> SEQ ID NO 2
<211> LENGTH: 33
<212> TYPE: DNA
```

```
<213> ORGANISM: Artificial Sequence
<220> FEATURE:
<223> OTHER INFORMATION: chemically synthesized nucleotide sequence of
      control BARP 6AA-6associated with normal growth and competency

<400> SEQUENCE: 2
atggcctgtg tgcgggtgtg gatggggtgt tag                              33

<210> SEQ ID NO 3
<211> LENGTH: 33
<212> TYPE: DNA
<213> ORGANISM: Artificial Sequence
<220> FEATURE:
<223> OTHER INFORMATION: chemically synthesized nucleotide sequence of
      control BARP RBS6AA-11 associated with normal growth and
      competency

<400> SEQUENCE: 3
atggcctgtt acaccggtca tgctacttgt tag                              33

<210> SEQ ID NO 4
<211> LENGTH: 51
<212> TYPE: DNA
<213> ORGANISM: Artificial Sequence
<220> FEATURE:
<223> OTHER INFORMATION: chemically synthesized nucleotide sequence of
      BARP 12AA-1, -3, and -4 associated with less blue phenotype

<400> SEQUENCE: 4
atgggctgtt ttcaacgaac cggttgtctt ggcacggtgc gatagtgtta g           51

<210> SEQ ID NO 5
<211> LENGTH: 51
<212> TYPE: DNA
<213> ORGANISM: Artificial Sequence
<220> FEATURE:
<223> OTHER INFORMATION: chemically synthesized nucleotide sequence of
      BARP 12AA-2, -5, -7, and -10 associated with mucoid growth and
      defects in autolysis

<400> SEQUENCE: 5
atgggctgtg tggcagggcc ctgcggcctg acggcgcgta acttttgtta g           51

<210> SEQ ID NO 6
<211> LENGTH: 51
<212> TYPE: DNA
<213> ORGANISM: Artificial Sequence
<220> FEATURE:
<223> OTHER INFORMATION: chemically synthesized nucleotide sequence of
      BARP 12AA-6 associated with mucoid growth and normal competency

<400> SEQUENCE: 6
atgggctgtt tccaaagtgt tcagcagctt cctctcgttc tcaaatgtta g           51

<210> SEQ ID NO 7
<211> LENGTH: 51
<212> TYPE: DNA
<213> ORGANISM: Artificial Sequence
<220> FEATURE:
<223> OTHER INFORMATION: chemically synthesized nucleotide sequence of
      BARP 12AA-11 associated with mucoid growth and normal competency

<400> SEQUENCE: 7
atgggctgtt atgggtcttt tacactacgt ttcatttgaa atgattgtta g           51

<210> SEQ ID NO 8
<211> LENGTH: 33
```

```
<212> TYPE: DNA
<213> ORGANISM: Artificial Sequence
<220> FEATURE:
<223> OTHER INFORMATION: chemically synthesized nucleotide sequence of
      BARP RBS6AA-1 associated with mucoid growth and normal competency

<400> SEQUENCE: 8
atggcctgta ttttatgcca tcaattatgt tag                              33

<210> SEQ ID NO 9
<211> LENGTH: 33
<212> TYPE: DNA
<213> ORGANISM: Artificial Sequence
<220> FEATURE:
<223> OTHER INFORMATION: chemically synthesized nucleotide sequence of
      BARP RBS6AA-10 associated with mucoid growth and normal competency

<400> SEQUENCE: 9
atggcctgtg ccctgttgt taataagtgt tag                               33

<210> SEQ ID NO 10
<211> LENGTH: 33
<212> TYPE: DNA
<213> ORGANISM: Artificial Sequence
<220> FEATURE:
<223> OTHER INFORMATION: chemically synthesized nucleotide sequence of
      BARP RBS6AA-12 associated with mucoid growth and normal competency

<400> SEQUENCE: 10
atggcctgtt gacaatttgt ccttaaatgt tag                              33

<210> SEQ ID NO 11
<211> LENGTH: 51
<212> TYPE: DNA
<213> ORGANISM: Artificial Sequence
<220> FEATURE:
<223> OTHER INFORMATION: chemically synthesized nucleotide sequence of
      BARP RBS12AA-5 associated with mucoid growth and less blue
      phenotype

<400> SEQUENCE: 11
atgggctgtt ttattgggtt cttgttccca cagtatgaac ttgtttgtta g          51

<210> SEQ ID NO 12
<211> LENGTH: 51
<212> TYPE: DNA
<213> ORGANISM: Artificial Sequence
<220> FEATURE:
<223> OTHER INFORMATION: chemically synthesized nucleotide sequence of
      BARP RBS12AA-9 associated with mucoid growth and less blue
      phenotype

<400> SEQUENCE: 12
atgggctgtc acacttttat ttaaccggct cagtcttgct gactatgtta g          51

<210> SEQ ID NO 13
<211> LENGTH: 10
<212> TYPE: PRT
<213> ORGANISM: Artificial Sequence
<220> FEATURE:
<223> OTHER INFORMATION: chemically synthesized peptide sequence of
      6AA-6, SEQ ID NO: 2

<400> SEQUENCE: 13

Met Ala Cys Val Arg Val Trp Met Gly Cys
1               5                   10
```

```
<210> SEQ ID NO 14
<211> LENGTH: 10
<212> TYPE: PRT
<213> ORGANISM: Artificial Sequence
<220> FEATURE:
<223> OTHER INFORMATION: chemically synthesized peptide sequence of
      RBS6AA-11, SEQ ID NO: 3

<400> SEQUENCE: 14

Met Ala Cys Tyr Thr Gly His Ala Thr Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: chemically synthesized peptide sequence of
      12AA-1, -3, and -4, SEQ ID NO: 4

<400> SEQUENCE: 15

Met Gly Cys Phe Gln Arg Thr Gly Cys Leu Gly Thr Val Arg
1               5                   10

<210> SEQ ID NO 16
<211> LENGTH: 16
<212> TYPE: PRT
<213> ORGANISM: Artificial Sequence
<220> FEATURE:
<223> OTHER INFORMATION: chemically synthesized peptide sequence of
      12AA-2, -5, -7, and -10, SEQ ID NO: 5

<400> SEQUENCE: 16

Met Gly Cys Val Ala Gly Pro Cys Gly Leu Thr Ala Arg Asn Phe Cys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: chemically synthesized peptide sequence of
      12AA-6, SEQ ID NO: 6

<400> SEQUENCE: 17

Met Gly Cys Phe Gln Ser Val Gln Gln Leu Pro Leu Val Leu Lys Cys
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: chemically synthesized peptide sequence of
      12AA-11, SEQ ID NO: 7

<400> SEQUENCE: 18

Met Gly Cys Tyr Gly Ser Phe Thr Leu Arg Phe Ile
1               5                   10

<210> SEQ ID NO 19
<211> LENGTH: 10
<212> TYPE: PRT
<213> ORGANISM: Artificial Sequence
<220> FEATURE:
<223> OTHER INFORMATION: chemically synthesized peptide sequence of
      RBS6AA-1, SEQ ID NO: 8

<400> SEQUENCE: 19
```

```
Met Ala Cys Ile Leu Cys His Gln Leu Cys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: chemically synthesized peptide sequence of
      RBS6AA-10, SEQ ID NO: 9

<400> SEQUENCE: 20

Met Ala Cys Ala Pro Val Val Asn Lys Cys
1               5                   10

<210> SEQ ID NO 21
<211> LENGTH: 16
<212> TYPE: PRT
<213> ORGANISM: Artificial Sequence
<220> FEATURE:
<223> OTHER INFORMATION: chemically synthesized peptide sequence of
      RBS12AA-5, SEQ ID NO: 11

<400> SEQUENCE: 21

Met Gly Cys Phe Ile Gly Phe Leu Phe Pro Gln Tyr Glu Leu Val Cys
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: chemically synthesized peptide sequence of
      RBS12AA-9, SEQ ID NO: 12

<400> SEQUENCE: 22

Met Gly Cys His Thr Phe Ile
1               5
```